United States Patent
Connors et al.

(10) Patent No.: US 6,193,711 B1
(45) Date of Patent: Feb. 27, 2001

(54) RAPID PULSED ER:YAG LASER

(75) Inventors: Kevin Connors, Palo Alto; Greg Spooner, San Francisco; Ralph Saunders, San Ramon, all of CA (US)

(73) Assignee: Coherent, Inc., Santa Clara, CA (US)

( * ) Notice: Subject to any disclaimer, the term of this patent is extended or adjusted under 35 U.S.C. 154(b) by 0 days.

(21) Appl. No.: 08/991,217

(22) Filed: Dec. 12, 1997

(51) Int. Cl.$^7$ .................................................. A61N 5/06
(52) U.S. Cl. .................. 606/12; 606/3; 606/10; 606/13; 372/25; 372/29; 372/34; 372/705
(58) Field of Search ................. 606/10–12, 19, 606/3; 372/9, 15, 22, 25, 28–31, 33, 34–36, 39–42, 66, 69, 70, 92, 98, 109, 705

(56) References Cited

U.S. PATENT DOCUMENTS

| | | | |
|---|---|---|---|
| 3,806,829 | * 4/1974 | Duston et al. | 372/25 |
| 5,023,886 | * 6/1991 | Hobart et al. | 372/99 |
| 5,321,715 | * 6/1994 | Trost | 372/25 |
| 5,363,387 | * 11/1994 | Sinofsky | 372/15 |
| 5,406,577 | * 4/1995 | Gagosz | 372/25 |
| 5,422,899 | 6/1995 | Freiberg et al. . | |
| 5,498,935 | 3/1996 | McMahan et al. . | |
| 5,644,585 | 7/1997 | Mitchell et al. . | |

FOREIGN PATENT DOCUMENTS

WO 96/41577   12/1996   (WO) ........................ A61B/17/36

* cited by examiner

Primary Examiner—David M. Shay
(74) Attorney, Agent, or Firm—Limbach & Limbach L.L.P.

(57) ABSTRACT

An Er:YAG laser system has a resonant cavity including an Er:YAG rod pulse-pumped by a pulsed flashlamp. The pump-pulse repetition rate and average power is selected to provide a known essentially constant thermal-lensing power in the Er:YAG rod. Design parameters of the Er:YAG rod and the resonant cavity are selected to compensate for this thermal-lensing power. A shutter in the resonant cavity, when closed or open, respectively prevents or allows a laser output-pulse to be generated in response to a pump-pulse. Laser output-pulse duration is continuously variable and is controlled by controlling the duration of flashlamp-pulses. A sequence of laser output-pulses is controlled by opening and closing the shutter. This arrangement has the advantage that the laser output-pulse repetition rate can be selected to be the flashlamp-pulse repetition rate or some sub-multiple thereof while maintaining thermal-lensing power in the rod essentially constant and compensated for.

24 Claims, 7 Drawing Sheets

RAPID PULSED ER:YAG LASER

TECHNICAL FIELD OF THE INVENTION

The present invention relates in general to pulsed solid-state lasers having output wavelengths in the mid-IR spectral region. The invention relates in particular to a rapid-pulsed erbium-doped YAG (Er:YAG) laser for use in medical procedures involving tissue ablation and incision.

DISCUSSION OF BACKGROUND ART

It has been known for some time that tissue ablation can be enhanced through the use of infrared wavelengths that more closely match absorption peaks of water, the major constituent in biological tissue. Accordingly, the industry has recently been exploring the use of erbium-doped gain media for medical applications. Erbium-doped YAG crystals will generate an output wavelength of about 2.9 micrometers ($\mu$m) which is matched to a prominent absorption peak in water. Er:YAG radiation can be particularly useful in cosmetic or aesthetic laser surgical applications such as skin resurfacing, as the high absorption coefficient for the radiation in water limits penetration depth of the radiation essentially to the skin.

In skin resurfacing, skin is removed by photoablation using a high energy pulse, for example, on the order of about 1 Joule (J). The pulse has a relatively short duration, for example about 200 to 500 microseconds ($\mu$s). Energy is applied in a beam having a diameter of about 2 to 3 millimeters (mm) at pulse rates between about 1 to 15 Hertz (Hz). The short pulse duration provides that no appreciable heat is generated, which limits collateral damage. The short penetration depth provides that healing (new skin growth) can be complete in about two weeks or less.

The short penetration depth of Er:YAG radiation is also potentially attractive for cosmetic procedures which require skin incision in sensitive areas. An example of such a procedure is blepharoplasty, for rejuvenating the appearance of aging eyelids. This procedure requires an incision to be made very close to an eyelid, consequently a very precise cut is required. To make such a precise cut, an Er:YAG laser beam is preferably focussed to a much smaller spot, for example, about 200 to 300 $\mu$m in diameter. Focussing to a small spot provides not only the required precision, but provides that less energy per pulse is required to reach an ablation threshold intensity. These low energy pulses are preferably delivered at a relatively rapid repetition rate, for example, preferably at least 50 Hz, and more preferably about 100 Hz or even greater.

Erbium laser systems operable at up to about 30 Hz are commercially available. Attempts to increase the repetition rate above this level, however, have met with problems in obtaining adequate output power as well as problems with the thermal loading and accompanying thermal-lensing of the laser gain-medium (laser-rod). Thermal-lensing results from heating of the rod by the portion of absorbed pump-light which is not extracted as laser energy and can lead to instabilities of the laser resonator, and reduce the upper limit of pump-power.

One scheme for providing repetition rates of about 100 Hz in a single resonator with reduced instability is described in U.S. Pat. No. 5,644,585. This scheme, however, involves decreasing output power by increasing the reflectivity (decreasing transmission) of a resonant cavity. The higher reflectance of the output coupling mirror decreases the flashlamp power required to provide lasing, which in turn reduces thermal loading on the laser-rod. For operating at pulse rates higher than 200 Hz, without increasing thermal loading problems, the outputs of two or more resonant cavities are interleaved such that pulses from one resonant cavity are delivered in an interval between pulses from another resonant cavity. This of course leads to a system of significantly increased cost and complexity compared with single resonant cavity system.

There remains a need for a pulsed Er:Yag laser capable of providing a high quality beam of relatively low energy pulses at pulse repetition rates up to about 200 Hz or greater for providing smooth, precise incisions, but which can also provide controllable higher energy pulses at lower repetition rates down to about 1 Hz. Such a laser could be used for a wide range of surgical procedures, including large area operations such as skin resurfacing which typically require high pulse energy. This could significantly reduce the capital and maintenance cost of laser equipment for a surgeon, which in turn could lead to reduced operation costs and increased access to laser surgical procedures for patients.

SUMMARY OF THE INVENTION

Deficiencies of above described prior art Er:YAG laser systems are overcome in a Er:YAG laser system in accordance with the present invention by maintaining thermal-lensing power in the Er:YAG gain medium essentially constant in a predetermined range rather than attempting to limit thermal-lensing power by limiting pump-power to the gain medium, and hence output-power of the system. This recognizes that it is changes in thermal-lensing power rather than thermal-lensing power itself that causes variations in output-beam characteristics of a laser resonator, and in the stability of such a resonator. A resonator can be designed to operate stably over a predictable range of thermal-lensing power by appropriate selection of gain-medium and resonator design characteristics. In a laser system in accordance with present invention an essentially constant time-averaged pump-power can be maintained while varying output-pulse power and repetition rate, within controllable limits. This provides that the gain medium can be strongly pumped for providing high energy output pulses.

In one aspect of the present invention, an Er:YAG laser system is arranged such that an Er:YAG gain medium in a resonant cavity is flashlamp pulse-pumped at constant average pump-power and at a pulse repetition rate which maintains a predetermined thermal-lensing effect in the gain-medium, while the energy-per-pulse of selected laser output-pulses of the resonant cavity is also maintained constant. Design characteristics of the resonant cavity and the gain medium are selected to compensate for the predetermined thermal-lensing effect.

In a preferred embodiment of the inventive laser system, laser output-pulse repetition rate of the resonator is controlled by controlling the flashlamp-pulse (exciting-pulse) repetition rate, and by providing a shutter in the resonant cavity which, when closed, prevents, and when open, allows generation of a laser output-pulse in response to a flashlamp-pulse. Laser output-pulse energy is controlled by controlling the duration of flashlamp-pulses which are allowed by the shutter to generate a laser output-pulse.

In another aspect of the present invention, the flashlamp is powered by a power supply including reservoir-capacitor bank, charged at a selected, essentially constant voltage, the reservoir-capacitor bank is connected to the flashlamp via a switch which controls the repetition rate and duration of flashlamp-pulses. Maintaining the capacitor bank at a constant voltage provides that pulse-current through the lamp is controlled at a selected, essentially constant level.

This arrangement allows that output-pulse energy can be varied from about 20 millijoules (mJ) to 3 Joules (J), and that output-pulse repetition rate can be varied from about 1 Hz to more than 200 Hz, all at an essentially constant average flashlamp-power on the order of 1 kilowatt (KW), while maintaining an essentially constant thermal-lensing power in the gain medium. Maintaining constant thermal-lensing power in turn provides for very stable operation, and an essentially constant output-beam divergence and beam propagation factor $M^2$.

In yet another aspect of a laser system in accordance with the present invention, providing a stable controllable output-beam divergence makes the system particularly compatible with articulated-arm delivery of the laser output-pulses to tissue to be treated. Articulated arm delivery is preferred for the 2.94 $\mu$m radiation of an Er:YAG laser. Such an arm is typically formed from tubular sections. The tubular sections are joined by swivel joints which contain reflective optics for steering, and optionally focussing, a laser beam through the arm. Because of this, it can have very low loss characteristics and operate with much higher power beams compared with a fiber delivery system. A fiber delivery system, however, can tolerate a relatively wide variation of input-beam divergence within the angular acceptance of the fiber without varying the form of the output-beam.

The quality of a beam at the output end of an articulated arm is directly dependent on the quality of the beam at the input end of the articulated arm. Variations in divergence of the input-beam will result in variations of energy density in the output-beam, which, in turn, will result in poor control of optical-radiation dosage at a treatment site. Articulated arm delivery can be used to deliver output-pulses from a laser in accordance with the present invention, while providing precise, controllable optical-radiation dosage at a treatment site. Those skilled in the art will recognize this and other advantages of the inventive laser system from the detailed description thereof presented hereinbelow.

BRIEF DESCRIPTION OF THE DRAWINGS

The accompanying drawings, which are incorporated in and constitute a part of the specification, schematically illustrate a preferred embodiment of the present invention, and together with the general description given above and the detailed description of the preferred embodiment given below, serve to explain the principles of the invention.

DETAILED DESCRIPTION OF THE INVENTION

Figure 1:
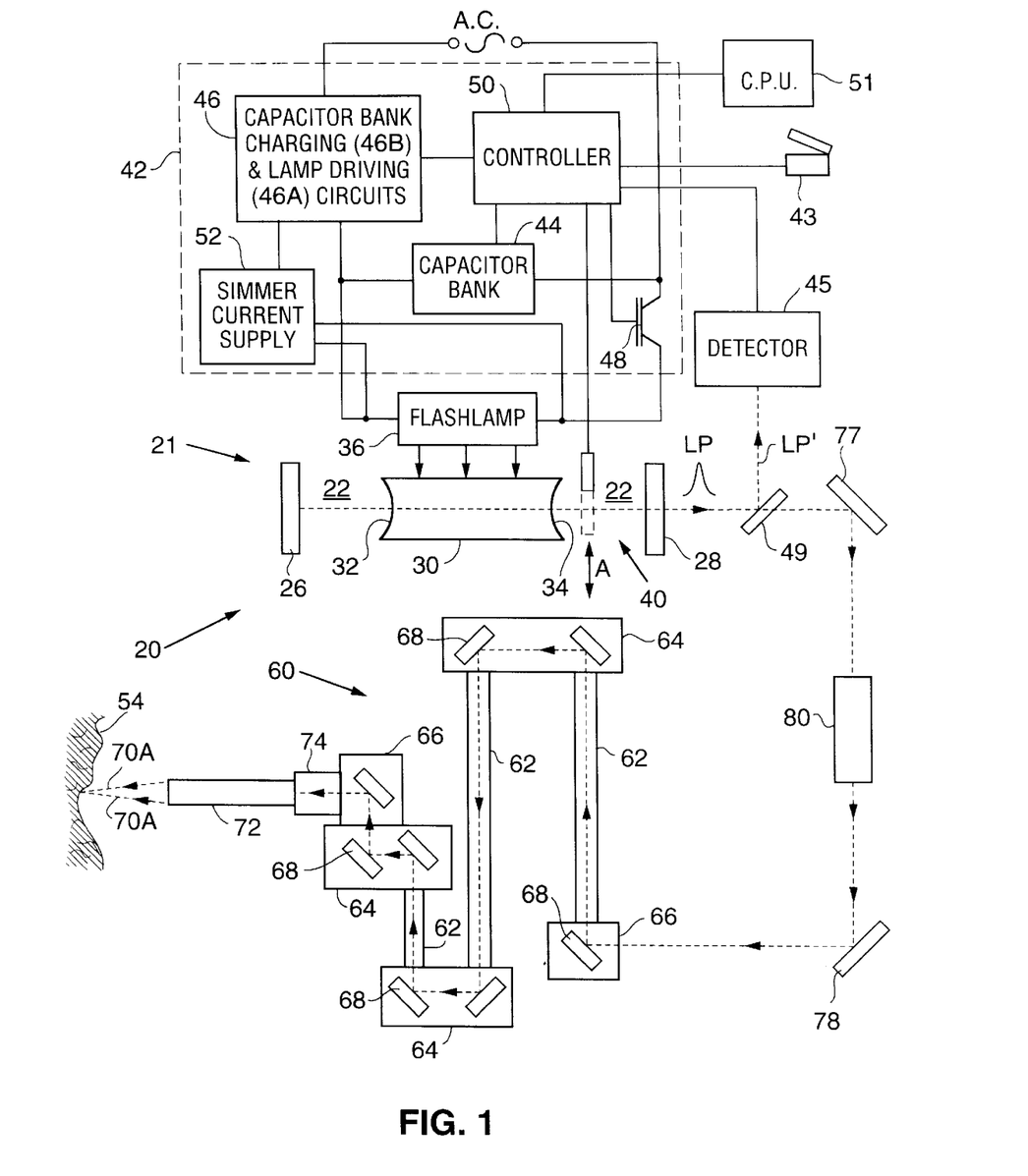
FIG. 1 schematically illustrates one preferred embodiment of a laser system in accordance with the present invention including a flashlamp-pumped gain medium in a resonant cavity, a power supply having a reservoir-capacitor bank for energizing the flashlamp and circuitry for charging the reservoir-capacitor bank, a shutter for selectively preventing or allowing generation of laser output-pulses by the resonant cavity, and an articulated arm for delivering laser output-pulses generated by the resonant cavity to biological tissue to be treated.

Turning now to the drawings, wherein like components are designated by like reference numerals, FIG. 1 schematically illustrates one preferred embodiment 20 of a laser system in accordance with the present invention. System 10 includes a laser 21 having a resonator 22 terminated by a highly reflecting mirror 26 and a partially-transmitting, output-coupling mirror 28. Located in resonator 22 is an Er:YAG gain-medium (rod) 30 having end faces 32 and 34.

Rod 30 is optically-pumped by a flashlamp 36. Flashlamp 36 delivers pump-light (indicated by arrows P) in a repeated sequence of flashlamp-pulses (exciting-pulses), at least one of which has sufficient energy to excite gain rod 30 above a threshold level required to provide laser action in resonator 22. The sequence of pulses is preferably selected such that each pulse has an essentially constant peak power. The term "essentially", in this regard, meaning within practical limits of electronic control. Relative energy of pulses in the pulse-sequence is preferably determined by pulse duration. The energy and spacing of pulses in the pulse sequence is selected such that thermal-lensing power in the rod remains essentially constant. The term "essentially", in this regard, meaning that the thermal-lensing can be defined as having a steady "DC" component but may include fluctuations, traceable to individual flashlamp-pulses, which are either small compared to the steady component, or occur in a time period sufficiently short that the generation of laser pulses is not affected. This is achieved by providing that the flashlamp-pulse repetition rate is greater than the thermal relaxation rate of the rod, such that thermal-lensing is determined primarily by the average residual pump-power in the rod, and any cooling mechanism of the rod. A flashlamp-pulse repetition rate greater than about 10 Hz is preferred.

In one preferred arrangement of a laser 21, mirrors 26 and 28 are plane mirrors twenty-seven centimeters (27.0 cm) apart. Rod 30 is 9.0 cm long and with end-faces 32 and 34 thereof each being concave, having a radius of curvature of 30.0 cm. Er:YAG is a particularly strong thermal-lensing material having a thermal-lensing effect more than an order of magnitude greater than Nd:YAG. This arrangement is designed to compensate for a thermal-lensing dioptric-power of about ten diopters in rod 30 which results when flashlamp 36 is driven at an average power of about 1.0 KW.

A shutter 40 can be inserted into or removed from the resonator as illustrated in FIG. 1 by arrows A. In its inserted or "closed" position (illustrated in phantom in FIG. 1), laser action in resonator 22 is prevented under any circumstances. When shutter 40 is in a retracted or "open" position, a laser output-pulse (LP) will be generated in response to any flashlamp-pulse having sufficient energy to excite gain-medium 30 above the lasing threshold level. A fraction LP' of each output-pulse is "picked-off" by a beamsplitter 49 and directed to a detector 45, the output of which is used for output-power and thermal-lensing control schemes, described in detail hereinbelow.

Flashlamp 36 is preferably driven by a reservoir-capacitor type power supply 42. In power supply 42, a capacitor bank 44 is charged at a selectable constant voltage preferably between about 400 and 800 volts (V) by a charging circuit 46. Charging circuit 46 includes a rectifier arrangement for rectifying the A.C. (wallplug) input to the power supply, and an inductive charging circuit which allows capacitor-bank 44 to be charged at any voltage, from a minimum determined by the half-wave rectification voltage of the A.C. input, to any safe maximum determined by the durability of electronic components of the circuit.

Capacitor bank 44 is connected to or disconnected from flashlamp 36 via a transistor switch 48, which is preferably an IGBT. A controller 50 operates switch 48 in a manner which determines the duration of flashlamp-pulses and spacing therebetween. Controller 50 also controls the operation of shutter 40 as well as switch 48. A central processing unit (CPU) 51 sends commands to the controller and receives measurements from the controller for control purposes. In a ready-mode of laser 21, before and between delivery of operative pulse sequences, shutter 40 is in a closed position. A footswitch 43 is operated by an operator to initiate delivery of an operative pulse sequence, whereupon controller 50 takes over operation of shutter 40 according to commands provided by CPU 51 until footswitch 43 is operated to end the operative sequence.

A "simmer-current" supply 52 remains connected to flashlamp 36 constantly supplying sufficient current to the flashlamp to maintain a plasma therein, so that the flashlamp is able to respond essentially immediately to any current-pulse delivered by switch 48 from capacitor-bank 44.

It should be noted here that any glow associated with the simmer-current plasma provides a relatively small contribution to thermal-lensing compared with that provided by flashlamp-pulses. It should also be noted that simmer-current supply 52 is shown separately, here, merely for functional discussion. Practically, simmer-current supply 52 is preferably incorporated as part of an overall power supply architecture, as discussed further hereinbelow.

Capacitor bank 44 preferably is preferably arranged to store at least about ten times the electrical energy required to provide the most energetic flashlamp-pulse contemplated. Recharging the capacitor bank at least at the rate at which it is being depleted by current-pulse demand ensures that the voltage across the capacitor remains essentially constant, for example, within about ten percent of a target level.

The above-described arrangement of power supply 42 provides current-pulses having a rise-time of less than about 50 μs, which is significantly less than current rise-time possible with a more commonly used pulse-forming network (PFN) type power supply. Such a rapid current rise-time provides that pulses of a even relatively very short duration, for example about 200 μs, have an average current which is close to the peak current. Further details of power supply 42 and the manner in which it is controlled are presented further hereinbelow.

Laser output-pulses from resonator 22 are preferably delivered to tissue 54, for cutting heating or ablation thereof, by an articulated arm 60. Articulated arm 60 includes straight tubes 62, and swivel joints 64 and 66 including respectively one and two plane turning mirrors 68. The path of a laser beam through delivery arm 60 is indicated by broken line 70. Output-pulses from resonator 22 may be injected directly into articulated arm 60 via turning mirrors 77 and 78, or, optionally, via an a focal beam-expanding or beam-contracting telescope 80.

A handpiece 72 is connected to delivery arm 60 by means of an adaptor 74. Handpiece 72 includes focussing optics (not shown) for focussing beam 70 on a target 54 as indicated by arrows 70A. Delivery arm 60 preferably does not include any optical elements having optical-power. As such, provided beam 70 has a sufficiently narrow divergence, delivery arm 60 may be used with a wide range of handpieces of different optical power for performing different laser-surgical operations. In the absence of the thermal-lensing control advantages of the inventive laser, at the pump-power contemplated therefor, the beam would diverge too much to allow satisfactory propagation through the articulated arm.

Figure 2:
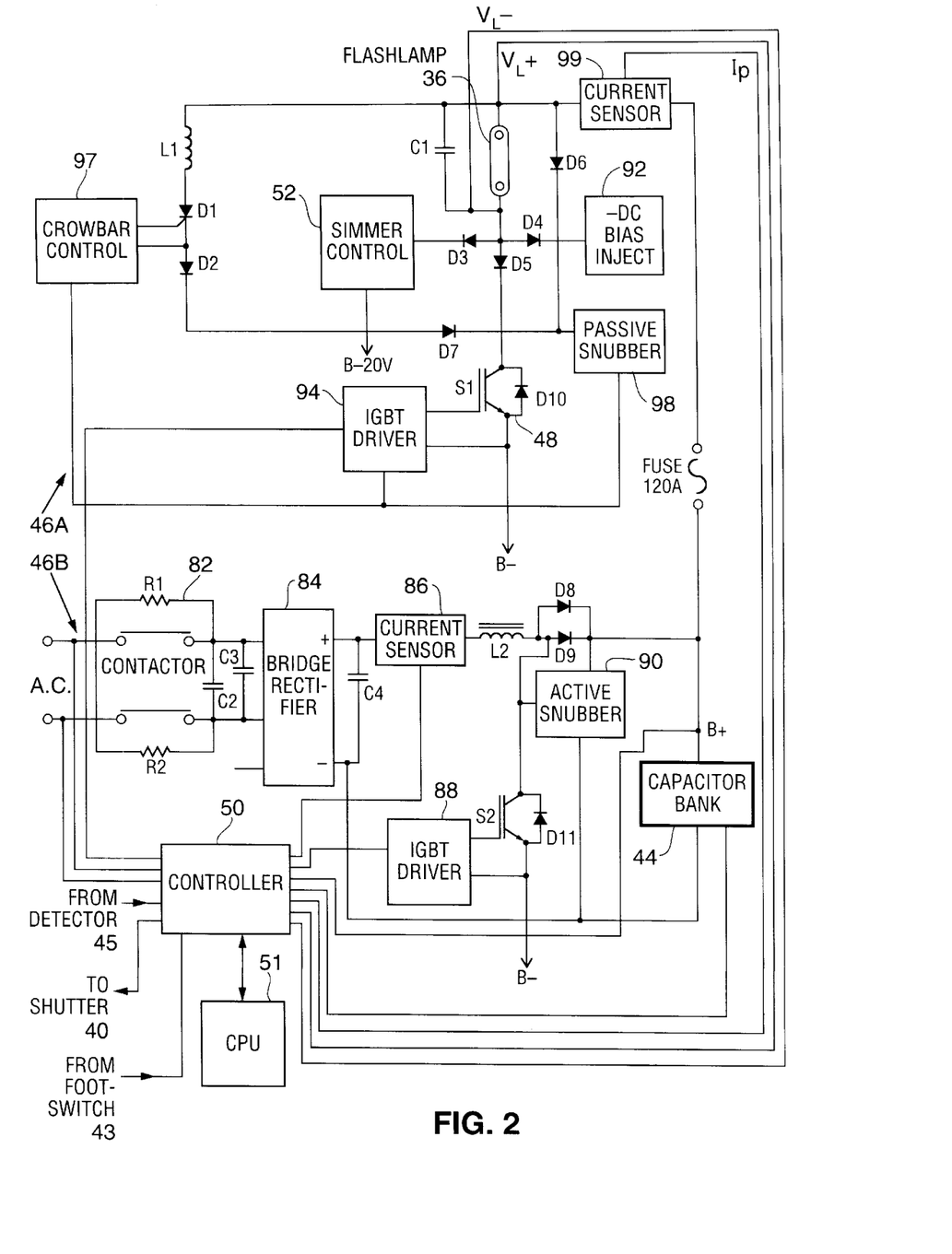
FIG. 2 is a combination circuit and block diagram schematically illustrating functional and control elements and connections therebetween in the power supply of FIG. 1.

Referring now to FIG. 2, details of a preferred circuit layout for power supply 42 are illustrated. This layout is configured to drive flash lamp 36 at a power of between about 200 W and 2.0 KW. For the above discussed resonator dimensions and gain medium configuration a preferred flashlamp-power is 1 KW. As the function of many components, such as diodes and capacitors, will be well known to those skilled in the electronic art from perusal of the circuit diagram alone, only the function of those components important to inventive aspects of the operation and control of laser 21 are discussed herein.

Beginning with charging circuitry 46B, for capacitor bank 44, AC power is provided via a "soft contactor" 82 to a bridge-rectifier 84 which outputs full-wave rectified 280 V DC, to a charging inductor L2. A current-sensor 86 monitors the output waveform of rectifier 84 and communicates this to controller 50. This information is used by controller 50 to ensure that charging of capacitor bank 44 always occurs at a preselected phase of this waveform. A transistor switch S2 (preferably an IGBT) controls deposition of charge stored in inductor L2 into capacitor bank 44. Capacitor bank 44 preferably has a capacity of about 2500 J, in anticipation of a maximum energy per current-pulse of 150 J for flashlamp 36. The target constant voltage (B+) for capacitor bank 44 is between 400 and 800 volts and is determined by CPU 51 according to power requirements of flashlamp 36. The target voltage is communicated to capacitor bank 44 from central processing unit 51 bank via controller 50. The actual voltage is sensed by controller 50. and used to determine when charge should be added. Operation of switch S2 is effected by controller 50 via a IGBT driver or boost-phase power-factor controller (BPFC) 88. Active snubber 90 includes circuitry which protects switch S2 against voltage overshoot on turn-off, and diodes D8 and D9 against current under-shoot at turn-on of switch S2.

Continuing now with reference to FIG. 2, driving circuitry 46A for flashlamp 36 is next discussed. Negative DC bias circuitry 92 provides that voltage across flashlamp 36, before it is "started", is about twice the voltage B+ at which it will be controlled during operation. Once the lamp is started, it is isolated from this negative DC bias by diode D4. Also, once flashlamp 36 is started, a minimum current (the simmer-current) of about 0.15 amperes (A), through the lamp, is controlled by simmer-control circuitry 52. Current through the lamp during a current-pulse is determined and controlled by the controlling of voltage B+. Current-pulses are generated when switch 48 connects flashlamp 36 to and disconnects it from capacitor bank 44. Switch 48, is preferably an IGBT and is operated by controller 50, on instructions from CPU 51, via IGBT driving circuitry 94. Passive snubber 98 includes circuitry which protects switch Sl from voltage overshoot at turn-off thereof.

For control of a pulse sequence, voltage developed across flashlamp 36 during a current-pulse is monitored ($V_L+$ and $V_L-$). Pulse current ($I_p$) is also monitored by a current-sensor 99. These two monitored parameters are real-time multiplied and integrated in controller 50. CPU 51 outputs an integrated energy request which is communicated to controller 50. When monitored output-pulse energy accumulates to the selected level, the current pulse is terminated and flashlamp 36 is returned to simmer-current. The electrical-pulse energy used is communicated to 51.

Crowbar control 97 is an electronic fast-shutter used by safety electronic circuitry (not shown). The function of crowbar control 97 is to provide an independent means of terminating a current-pulse to flashlamp 36. Crowbar control 97 is only used if any elements of controller 50 fail and do not turn off that current-pulse.

Figure 3A:
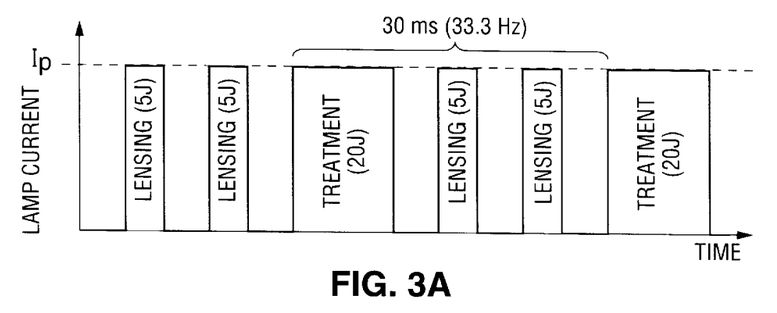
FIGS. 3A–C are graphs schematically illustrating a flashlamp-pulse sequence, shutter status and corresponding laser output-pulse sequence in one preferred mode of operation of a laser system in accordance with the present invention, providing relatively high energy tissue-ablating output-pulses at a pulse-repetition rate of about 30 Hz.
Figure 3B:
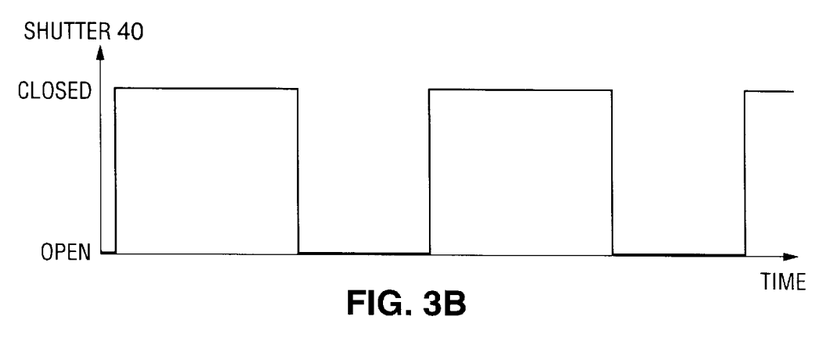
Figure 3C:
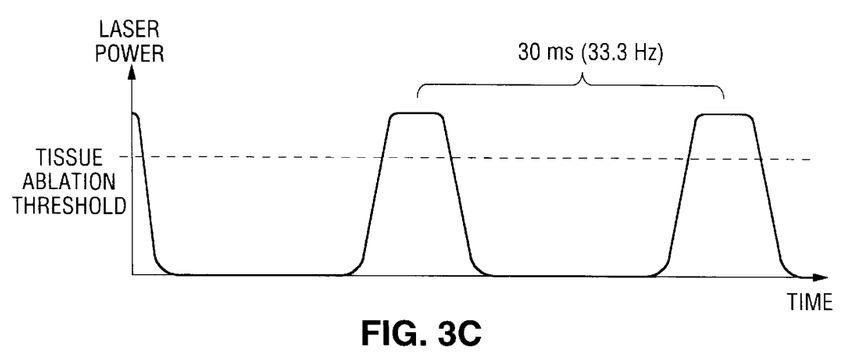

Referring now to FIGS. 3A–C, one example of an operating mode of laser 21 is graphically depicted. This mode provides a laser output-pulse sequence suitable, for example for skin resurfacing treatment. Here, flashlamp output (FIG. 3A) comprises a repeated sequence of three pulses. A first thereof is sufficiently energetic, for example about 20 J, to generate a laser output-pulse in an unobstructed resonator. This may be defined as a treatment current-pulse, bearing in mind, of course, that it also contributes to thermal-lensing. Following the treatment current-pulse are two thermal-lensing pulses of lesser energy, for example about 5 J, the only purpose of which is to provide (in combination with the 20 J pulse) a desired level of thermal-lensing for which resonator 22 is compensated. The sequence of three pulses repeats at intervals of 30 ms, i.e., at 33.3 Hz. The two thermal-lensing pulses are 10 ms apart. Pulse current $I_p$ is maintained essentially constant, determined by the constant voltage of capacitor-bank 44.

During the thermal-lensing pulses, shutter 40 is in a closed position so no lasing action is allowed even if the energy in the thermal-lensing pulses is sufficient to provide lasing action in an unobstructed resonator. So the laser power output of resonator 22 (FIG. 3C) is a train of equally-spaced, equally-energetic output-pulses, delivered at a repetition rate of 33.3 Hz. Flashlamp 36, however, is delivering exciting-pulses to rod 30 at a rate of 100 Hz.

In one preferred method of determining the pulse sequence of FIGS. 3A–C, the number and duration of thermal-lensing pulses is determined by CPU 51 on the basis that thermal-lensing-power in gain-medium 30 is directly related to the average power at which flashlamp 36 is being driven. In this method, a required laser-energy per treatment-pulse, treatment pulse duration, and repetition rate is user determined and communicated to CPU 51. CPU 51 instructs controller 51 to increase the corresponding flashlamp current-pulse energy until the required laser-energy per treatment-pulse is detected. Computed current-pulse power for providing the desired treatment pulses is subtracted from the target lamp-power that provides thermal-lensing power for which resonator 22 is compensated. In the above and other examples described herein, this is assumed to be 1 KW. CPU 51 then determines a number and duration of current-pulses, about equally spaced in time, which will provide the target flashlamp power consumption.

The above described thermal-lensing pulse computation occurs continuously during an operation. This provides that energy of thermal-lensing current-pulses can be continuously adjusted from the initially set nominal values, to values required to compensate for any changes in current-pulse energy required to maintain a constant output-pulse energy in corresponding laser output-pulses. Such changes may be required as a result of variations in efficiency of laser 21 which may occur during the operation period. CPU 51 is programmed such that a user is not allowed to initiate a pulse sequence, for which thermal-lensing control at the compensated level is not possible.

Figure 4A:
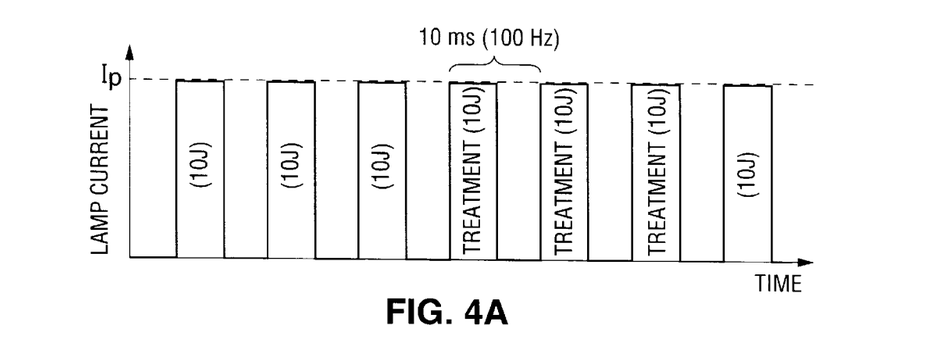
FIGS. 4A–C are graphs schematically illustrating a flashlamp-pulse sequence, shutter status and corresponding laser output-pulse sequence in another preferred mode of operation of a laser system in accordance with the present invention, providing relatively low energy tissue-ablating output-pulses in a regular sequence at a rate of 100 Hz.
Figure 4B:
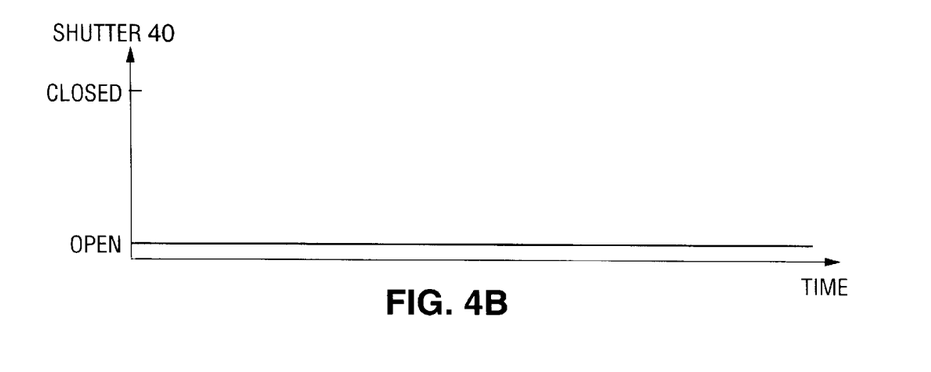
Figure 4C:
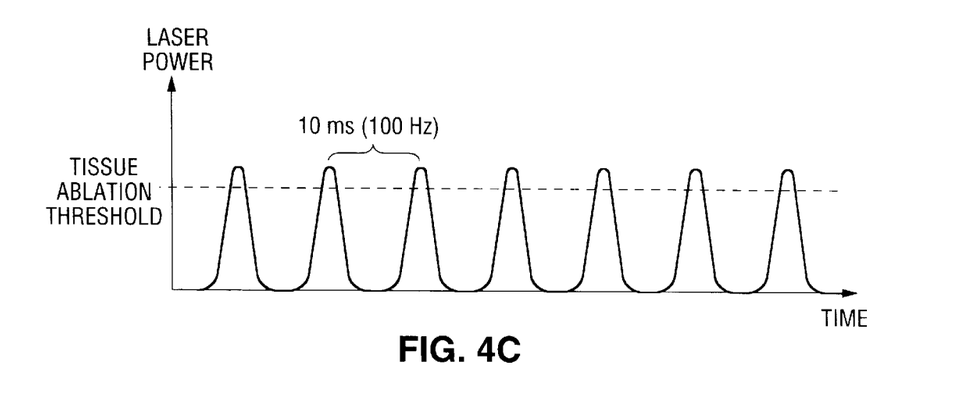

Referring now to FIGS. 4A–C, another example of an operating mode of laser 21 is graphically depicted. This operating mode is particularly suited for an operation such as a blepharoplasty, which requires a fine incision to be made in tissue around the upper or lower eyelid. For this, a rapid train of relatively low energy output-pulses is preferred. A treatment beam is focussed to a small spot at thereby creating power density over the tissue ablation threshold to produce an incision with a clean, smooth edge, only the required depth, and minimal collateral damage.

In this mode, current-pulses of equal energy, for example of nominally about 10 J energy, are delivered to the flashlamp at equal intervals of 10 ms, i.e., at 100 Hz repetition rate (FIG. 4A). Each of the pulses is sufficiently energetic to provide laser action. Because the current in each pulse is maintained constant and the 100 Hz delivery rate is sufficiently high, each of the pulses contributes equally to thermal-lensing in rod 30.

Shutter 40 is held in an open position throughout the period of operation (FIG. 4B). This results in the delivery of laser output-pulses at the same rate as flashlamp current-pulses (FIG. 4C).

One disadvantage of operating mode of FIGS. 4A–C is that, as all current-pulses contribute equally to thermal-lensing, operational changes in efficiency of laser 21 are preferably compensated, for thermal-lensing control purposes, by adjusting the treatment-pulse repetition rate. In most operations, such adjustments will occur within tolerable limits of repetition-rate variation. However, should a fixed treatment pulse repetition-frequency be desired, another mode of operation is possible. A description of this mode is set forth below with reference to FIGS. 5A–C.

Figure 5A:
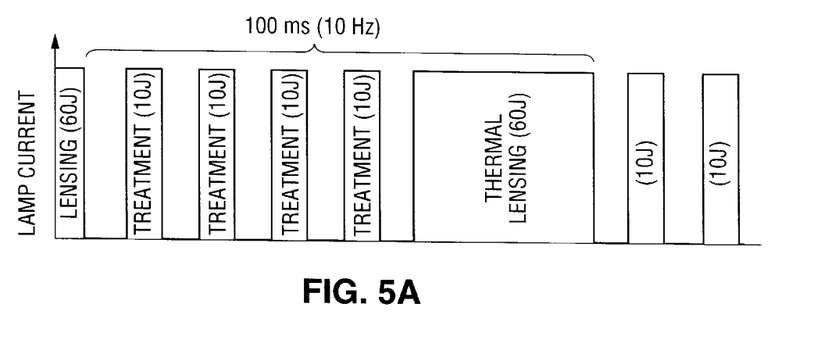
FIGS. 5A–C are graphs schematically illustrating a flashlamp-pulse sequence, shutter status and corresponding laser output-pulse sequence in yet another preferred mode of operation of a laser system in accordance with the present invention, providing relatively low energy tissue-ablating output-pulses in repeated trains at an effective pulse-repetition rate of 40 Hz.
Figure 5B:
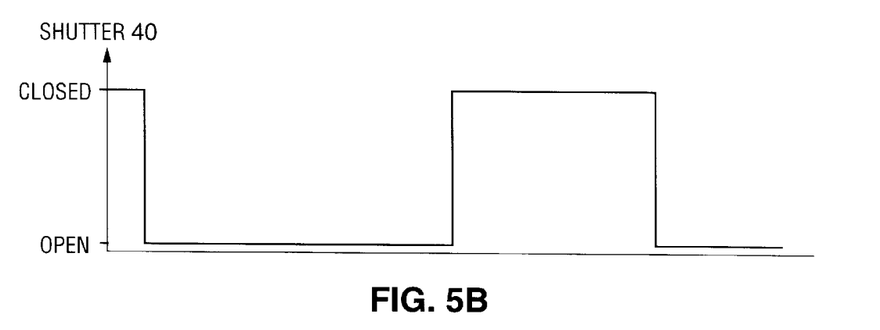
Figure 5C:
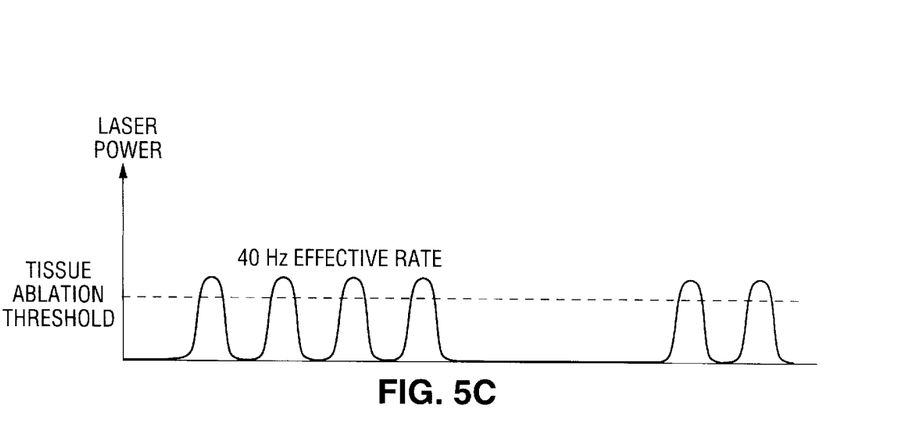

FIG. 5A depicts a sequence of five current-pulses, comprising four relatively low energy (nominally 10 J) treatment current-pulses followed by one nominally 60 J thermal pulse. The pulse sequence duration is 100 ms, requiring 1 KW flashlamp power. Shutter 40 is closed during delivery of the 60 J pulse (FIG. 5B), which is used only for thermal-lens compensation. Some number of lower energy pulses may be optionally substituted for the 60 J pulse. In the operating mode of FIGS. 5A–C, the energy of a thermal-lensing pulse or pulses is determined by subtracting the instant flashlamp current-pulse energy required to generate the treatment-pulses (which is set by a target laser output-pulse and a fixed repetition rate), from the target flashlamp operating power.

In this example, the net pulse-repetition rate (FIG. 5C) of laser output pulses is 40 Hz, although each output-pulse train in a sequence, here, is delivered at a significantly faster repetition rate.

While the ability of the Er:YAG radiation to provide ablation without significant collateral thermal-damage is of advantage in many laser surgical operations, it is believed that in skin resurfacing operations, some heating of the skin accompanying ablation can shrink collagen, thereby tightening the skin and promoting rapid growth of new collagen to speed post-operative healing. The flexibility and controllability of Er:YAG laser pulses deliverable by an Er:YAG laser in accordance with the present invention make it ideally suited for such a combination ablation and heating operation. One preferred example of an operating mode of laser 21, suitable for such an operation is schematically depicted in FIGS. 6A–C.

Figure 6A:
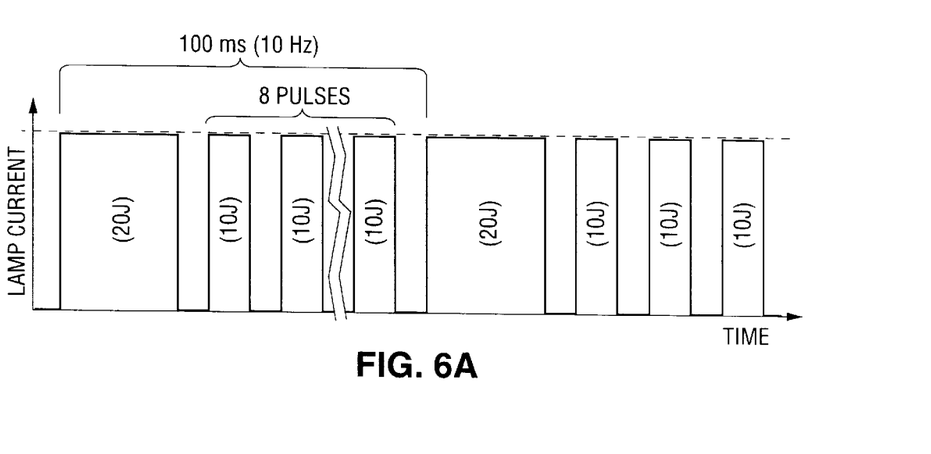
FIGS. 6A–C are graphs schematically illustrating a flashlamp-pulse sequence, shutter status and corresponding laser output-pulse sequence in still another preferred mode of operation of a laser system in accordance with the present invention, providing an output-pulse sequence including tissue-ablating output-pulses at a rate of 10 Hz interspersed with non-ablating output-pulses at a rate of 150 Hz.
Figure 6B:
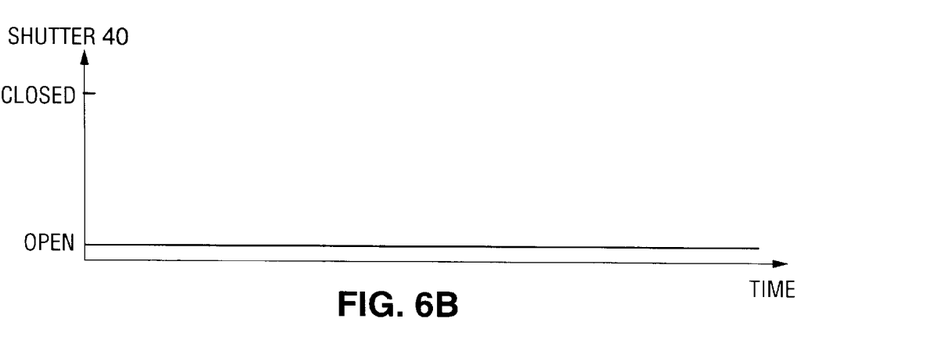
Figure 6C:
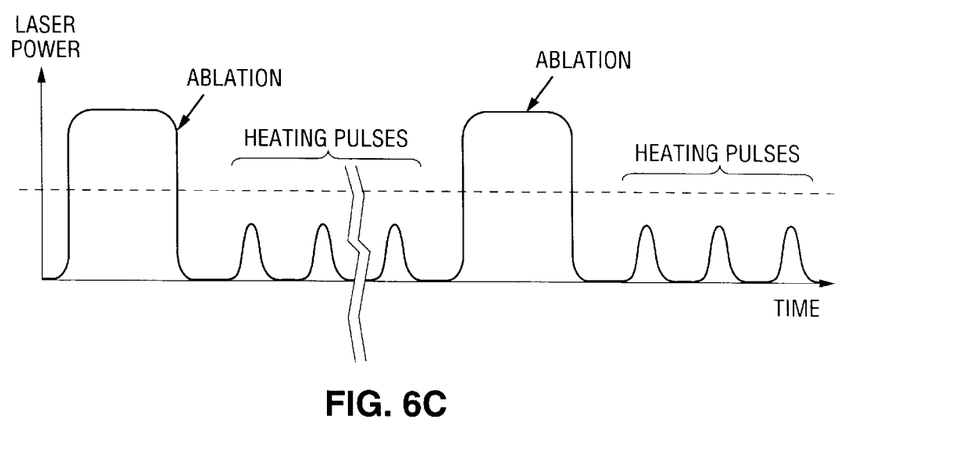

FIG. 6A depicts a repeated, 100 ms-long sequence of current-pulses to flashlamp 36. The sequence begins with a nominally 20 J pulse followed by eight nominally 10 J pulses (only 3 shown). Each pulse has sufficient energy to cause laser action, and shutter 40 is always in an open position (FIG. 4B). Referring to FIG. 6C, the 20 J current-pulse results in a laser output-pulse above the tissue ablation threshold, while the 10 J current-pulses result in laser output-pulses which provide only heating of tissue. As in other above-described examples the current-pulse sequence is designed to require 1 KW of power for driving flashlamp 36. In this mode, operational variations in efficiency of laser 21 are compensated by adjusting energy of the current-pulses which are used to generate the ablative laser output-pulse, thereby maintaining ablative laser pulses at a constant energy. A corresponding change in frequency and/or energy of current-pulses used to generate the sub-threshold output-pulses is used to maintain driving power of flashlamp 36 at the target 1 KW for thermal-lensing control. In cases where a variation in the energy delivered by heating pulses is not desirable, another operating mode of laser 21 can be provided which allows the energy of both ablative and thermal laser output-pulses to be held constant. One such mode is describe below with reference to FIGS. 7A–C.

Figure 7A:
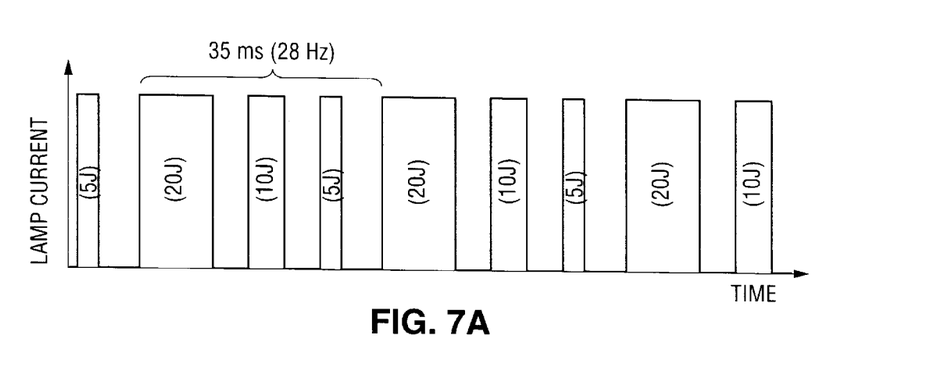
FIGS. 7A–C are graphs schematically illustrating a flashlamp-pulse sequence, shutter status and corresponding laser output-pulse sequence in a further preferred mode of operation of a laser system in accordance with the present invention, providing an output-pulse sequence including a tissue-ablating output-pulse followed by a non-ablating output-pulses at a sequence-repetition rate of 28 Hz.
Figure 7B:
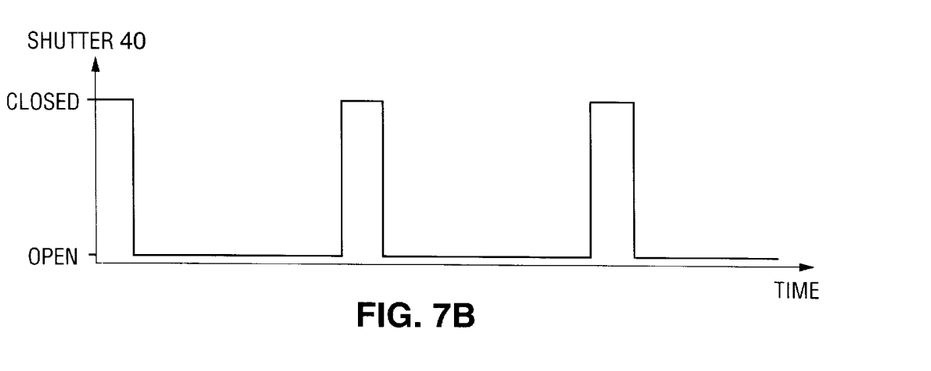
Figure 7C:
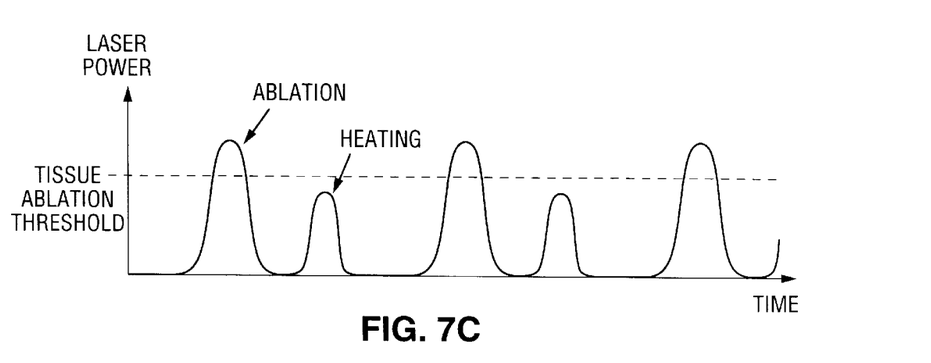

In FIG. 7A, a 35 ms-long sequence of flashlamp current-pulses includes a 20 J pulse followed, in order, by a 10 J pulse and a 5 J pulse. From FIG. 7C, it can be seen that the 20 J and 10 J pulses are delivered with shutter 40 open (FIG. 7B) to generate respectively an ablative laser output-pulse. and a sub threshold laser output-pulse for heating. The 5 J pulse of FIG. 7A is used only for thermal-lensing. Both the ablative and laser-output-pulses are controlled to target specifications, and the energy of corresponding current-pulses is varied to compensate for any changes in laser efficiency and thereby maintain these output pulses at specified values. The current-pulse responsible for thermal-lensing is varied from its nominal value, to zero if necessary, to maintain flashlamp power at the target 1 KW constant value.

It should be noted that in using any of the above-described operating modes, flashlamp 36 is preferably driven in a "ready" mode at 1 KW, with shutter 40 closed, immediately prior to and while the system is not in use for short periods between actual surgical operation. This may be effected by running at the selected current-pulse sequence or some other 1 KW sequence with shutter 40 closed. Such a ready mode provides that control of laser output-pulses is effective essentially from the first output-pulse delivered to tissue being treated.

In most cases, the above-discussed and similar pulse sequences can be effectively controlled by assuming a direct, essentially linear relationship between flashlamp power and thermal-lensing in gain medium 30. Thermal-lensing, however, results from the fraction of power absorbed by gain medium 30 which is not converted to laser light, and this fraction may vary with factors such as pump-power and pulse repetition rate. Those skilled in that art will recognize, without further description, that this fraction and any variations thereof may be readily determined by experiment. Should more accurate thermal-lensing control be required, this data may be provided to CPU 51 and used in determining above-discussed initial current-pulse sequences and operational corrections thereof.

The Er:YAG laser system of the present invention should not be considered limited by the embodiments described and depicted herein. Those skilled in the art may devise other embodiments and operating modes without departing from the spirit and scope of the present invention defined by the claims appended hereto.

What is claimed is:

1. A Er:YAG laser system for treating biological tissue, comprising:

an Er:YAG gain-medium located in a resonant cavity;

an optical pump for providing exciting-pulses in variable sequences thereof during an operational period of the laser system, one of said exciting-pulses in each said sequence each having sufficient energy to excite said gain-medium to a level sufficient to generate a laser output-pulse having sufficient energy to cause ablation of the biological tissue, all other exciting-pulses generation laser output-pulses having insufficient energy to cause ablation of said biological tissue but sufficient energy to cause heating of the biological tissue;

a power supply for providing current-pulses for repetitively energizing said optical pump, each of said current-pulses providing a said exciting-pulse;

a controller for controlling said power supply, said controller arranged such that during said operational period, energy-per-pulse in said ablation-causing laser output-pulse is actively maintained by said controller at a predetermined value by adjusting energy in a corresponding one of said exciting-pulses and responsive to said energy adjustment of said corresponding one of said exciting pulses one or both of energy and frequency of said all other exciting-pulses is correspondingly adjusted such that collectively all of said exciting-pulses cause an essentially constant predetermined, non-zero thermal-lensing effect in said gain-medium; and wherein design parameters of said resonant cavity and gain-medium are selected to compensate for said predetermined thermal-lensing effect in said gain-medium.

2. The laser system of claim 1, wherein said essentially constant thermal-lensing effect is achieved by controlling time-averaged power in all of said current-pulses at an essentially constant value.

3. A Er:YAG laser system for treating biological tissue, comprising:

an Er:YAG gain-medium located in a resonant cavity;

an optical pump for providing exciting-pulses in variable sets of at least one thereof during an operational period of the laser system, at least one of said exciting-pulses in each said set having sufficient energy to excite said gain-medium to a level sufficient to generate a laser output-pulse;

a power supply for providing current-pulses for repetitively energizing said optical pump, each of said current-pulses providing a said exciting-pulse;

a controller for controlling said power supply, said controller arranged such that during said operational period, energy-per-pulse in said laser output-pulse is actively maintained by said controller at a predetermined value by adjusting energy of said at least one of said exciting-pulses, and such that other said exciting-pulses are adjusted by said controller, responsive to said energy adjustment of said at least one of said exciting pulses, in at least one of energy-per-pulse or pulse-repetition frequency such that collectively all of said exciting pulses cause an essentially constant predetermined, non-zero thermal-lensing effect in said gain-medium; and wherein design parameters of said resonant cavity and gain-medium are selected to compensate for said predetermined thermal-lensing effect in said gain-medium.

4. The laser system of claim 3, wherein said power supply includes a reservoir capacitor bank and said controller is arranged such that said reservoir capacitor bank is maintained charged at an essentially constant voltage during an operational period of the laser system.

5. The laser system of claim 3, wherein said current-pulses have an essentially-constant peak current.

6. The laser system of claim 3, wherein there is a plurality of pulses in each of said sequences of exiting pulses.

7. The laser system of claim 3 wherein a said repeated pulse sequence includes a plurality of said exciting-pulses only one of which has sufficient energy to cause a said laser output-pulse, and said controller adjusts the energy in said only one sufficiently-energetic exciting-pulse for controlling the energy-per-pulse of said laser-output-pulse at said predetermined value and adjusts the energy of all other exciting-pulses in said repeated sequence for causing said constant thermal-lensing effect.

8. The laser system of claim 3 wherein a said repeated pulse sequence includes a plurality of said exciting-pulses all of which has sufficient energy to cause a said laser output-pulse, and said controller adjusts the energy in only one of said exciting-pulses for controlling the energy-per-pulse of a corresponding said laser-output-pulse at said predetermined value and adjusts the energy and/or frequency of all other exciting-pulses in said repeated sequence for causing said constant thermal-lensing effect.

9. The laser system of claim 3 wherein a said repeated pulse sequence includes a plurality of said exciting-pulses less than all of which have sufficient energy to cause a said laser output-pulse, and said controller adjusts the energy in said sufficiently-energetic exciting-pulses for controlling the energy-per-pulse of said laser-output-pulse at said predetermined value and adjusts the energy of all other exciting-pulses in said repeated sequence for causing said constant thermal-lensing effect.

10. The laser system of claim 3, further including an articulated arm for delivering said laser output-pulses to biological tissue to be treated.

11. The laser system of claim 10, wherein said articulated arm includes a plurality of hollow straight members connected by swivel-joint members, said swivel-joint members including reflective optical elements for guiding said laser-output-pulses through said hollow straight members.

12. The laser system of claim 3, wherein there is only one pulse in each of said sequences of exciting-pulses.

13. The laser system of claim 12 wherein said controller adjusts the frequency of said current-pulses for causing said constant thermal-lensing effect.

14. The laser system of claim 3 further including a shutter located in said resonant cavity, said shutter, in closed and open modes thereof, for respectively preventing and allowing generation of a laser output-pulse in response to a said exciting-pulse.

15. The laser system of claim 14, wherein said shutter and said power supply are cooperatively operated by said controller to provide laser output-pulses at a selectively variable repetition-rate while maintaining said essentially constant thermal-lensing effect in said gain medium.

16. The laser system of claim 15, wherein said output-pulse repetition-rate can be varied from about 1 Hz to more than 200 Hz.

17. The laser system of claim 16, wherein energy of said laser output-pulses can be varied from about 20 millijoules to 3 Joules.

18. A Er:YAG laser system for treating biological tissue, comprising:

an Er:YAG gain-medium located in a resonant cavity;

an optical pump for providing exciting-pulses in variable sequences of more than one thereof during an operational period of the laser system;

only one of said exciting-pulses in each said sequence each having sufficient energy to excite said gain medium to a level sufficient to generate a laser output-pulse;

a power supply for providing current-pulses for repetitively energizing said optical pump, each of said current-pulses providing a said exciting-pulse;

a controller for controlling said power supply, said controller arranged such that during said operational period, energy-per-pulse in said laser output-pulse is actively maintained by said controller at a predetermined value by adjusting energy in a corresponding said exciting-pulse and one or both of energy and frequency of all other exciting-pulses in a said sequence is adjusted by said controller, responsive to said energy adjustment of said at least one of said exciting pulses, such that collectively all of said exciting-pulses cause an essentially constant predetermined, non-zero thermal-lensing effect in said gain-medium; and wherein design parameters of said resonant cavity and gain-medium are selected to compensate for said predetermined thermal-lensing effect in said gain-medium.

19. The laser system of claim 18, wherein said essentially constant thermal-lensing effect is achieved by controlling time-averaged power in all of said current-pulses at an essentially constant value.

20. An Er:YAG laser system for treating biological tissue, comprising:

an Er:YAG gain-medium located in a resonant cavity;

an optical pump for providing exciting-pulses during an operational period of the laser system, each of said exciting-pulses having sufficient energy to excite said gain-medium to a level sufficient to generate a laser output-pulse;

a power supply for providing current-pulses for repetitively energizing said optical pump, each of said current-pulses providing a said exciting-pulse;

a controller for controlling said power supply, said controller arranged such that during said operational period, energy-per-pulse in each of said laser output-pulses is actively maintained by said controller at a predetermined value by adjusting the energy-per-pulse of corresponding said current-pulses and average power in said current-pulses is maintained by said controller at an essentially constant value by adjusting, responsive to said energy adjustment of said corresponding said exciting pulses, the repetition-frequency of said current-pulses, thereby maintaining an essentially constant predetermined, non-zero thermal-lensing effect in said gain-medium; and wherein design parameters of said resonant cavity and said gain-medium are selected to compensate for said predetermined thermal-lensing effect in said gain-medium.

21. A Er:YAG laser system for treating biological tissue, comprising:

an Er:YAG gain-medium located in a resonant cavity;

an optical pump for providing exciting-pulses for exciting said gain-medium;

a power supply for providing current-pulses for repetitively energizing said optical pump, each of said current-pulses providing a said exciting-pulse;

a controller arranged for controlling said power supply such that exciting-pulses are provided in variable sequences of more than one thereof during an operational period of the laser system, at least one said sequence of exciting-pulses in said sequences thereof having sufficient energy to excite said gain-medium to a level sufficient to generate a laser output-pulse;

a shutter located in said resonant cavity, said shutter, in closed and open modes thereof, for respectively preventing and allowing generation of a laser output-pulse in response to a said exciting-pulse having said sufficient energy;

said controller arranged for controlling said shutter cooperative with said power supply such that at least one of said plurality of exciting-pulses having sufficient energy to do so is allowed to generate a laser-output-pulse, and at least one of said exciting-pulses is prevented from generating a laser-output-pulse; and said controller arranged such that during said operational period, energy-per-pulse in at least one of said allowed laser output-pulses is actively maintained by said controller at a predetermined value by adjusting the energy in a corresponding said exciting-pulse and, by adjusting one or both of the repetition frequency or energy in all other said exciting pulses responsive to said energy adjustment of said corresponding said exciting-pulse provides that said exciting-pulses collectively cause an essentially constant predetermined, non-zero thermal-lensing effect in said gain-medium; and wherein design parameters of said resonant cavity and gain-medium being selected to compensate for said predetermined thermal-lensing effect in said gain-medium.

22. The laser system of claim 21, wherein said essentially constant thermal-lensing effect is achieved by controlling time-averaged power in all of said current-pulses at an essentially constant value.

23. The laser system of claim 21 wherein two of said exciting-pulses in each said sequence thereof each have sufficient energy to generate a laser output-pulse and are allowed by said shutter to generate two corresponding laser output-pulses, all other exciting-pulses in said sequence being prevented by said shutter from generating a laser output-pulse, and wherein said controller is further arranged to maintain energy-per-pulse in one of said two laser output-pulses at a first predetermined value and in the other of said two laser output-pulses at a second predetermined value.

24. The laser system of claim 23 wherein said first predetermined energy-per-pulse value is sufficient to cause ablation of the biological tissue and said second energy-per-pulse value is insufficient to cause ablation but sufficient to cause heating of the biological tissue.

* * * * *